(12) United States Patent
Chen et al.

(10) Patent No.: US 9,822,303 B2
(45) Date of Patent: *Nov. 21, 2017

(54) LIQUID CRYSTALS COMPRISING CYCLOPENTANE GROUPS

(71) Applicant: VVI BRIGHT CHINA LTD., Nanjing (CN)

(72) Inventors: Xinhua Chen, Erie, CO (US); R. Amaranatha Reddy, Boulder, CO (US)

(73) Assignee: VVI BRIGHT CHINA LTD, Nanjing (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/882,283

(22) Filed: Oct. 13, 2015

(65) Prior Publication Data

US 2016/0237348 A1 Aug. 18, 2016

Related U.S. Application Data

(63) Continuation of application No. 14/456,743, filed on Aug. 11, 2014, now abandoned, which is a continuation of application No. 12/866,295, filed as application No. PCT/US2009/033197 on Feb. 5, 2009, now Pat. No. 8,801,966.

(60) Provisional application No. 61/027,230, filed on Feb. 8, 2008.

(51) Int. Cl.
G02F 1/1333 (2006.01)
C09K 19/32 (2006.01)
C09K 19/30 (2006.01)
C07C 25/22 (2006.01)
C09K 19/34 (2006.01)

(52) U.S. Cl.
CPC ............ *C09K 19/322* (2013.01); *C07C 25/22* (2013.01); *C09K 19/30* (2013.01); *C09K 19/3405* (2013.01); *C07C 2601/08* (2017.05); *C09K 2019/3408* (2013.01); *Y10T 428/10* (2015.01)

(58) Field of Classification Search
CPC .. C09K 19/322; C09K 19/30; C09K 19/3405; C09K 2019/3408; Y10T 428/10; C07C 25/22; C07C 2601/08
USPC .......................... 252/299.01, 299.63; 428/1.1
See application file for complete search history.

(56) References Cited

U.S. PATENT DOCUMENTS

| 8,801,966 B2 * | 8/2014 | Chen | ...................... C09K 19/30 252/299.01 |
| 2015/0034872 A1 * | 2/2015 | Chen | ...................... C09K 19/30 252/299.62 |

* cited by examiner

*Primary Examiner* — Geraldina Visconti
(74) *Attorney, Agent, or Firm* — Lathrop Gage LLP

(57) ABSTRACT

Provided are liquid crystal compounds and mixtures incorporating the same. The liquid crystal compounds of the invention generally comprise a cyclopentane group and at least two other rings. In one embodiment, the liquid crystal compounds of the invention comprise a cyclopentane group and at least two other rings, one of which is a fused ring system.

15 Claims, No Drawings

LIQUID CRYSTALS COMPRISING CYCLOPENTANE GROUPS

CROSS-REFERENCE TO RELATED APPLICATIONS

This application is a continuation of U.S. patent application Ser. No. 14/456,743, filed Aug. 11, 2014 (now abandoned), which in turn is a continuation of U.S. patent application Ser. No. 12/866,295, filed Dec. 17, 2010, which issued as U.S. Pat. No. 8,801,966 on Aug. 12, 2014, and which is the US National Stage of International Application No. PCT/US2009/033197, filed Feb. 5, 2009, which claims the benefit of priority to U.S. Provisional Application Ser. No. 61/027,230, filed Feb. 8, 2008, each of which is hereby incorporated by reference to the extent not inconsistent with the disclosure herewith.

BACKGROUND OF THE INVENTION

Liquid crystal displays use mixtures of liquid crystals having desired material properties such as operating temperature range, thermal stability, light stability, switching time, and contrast ratio. The properties of the mixtures and devices are determined by the constituents of the mixtures.

The demand for liquid crystal displays having improved performance has increased. In particular, liquid crystal mixtures having low threshold voltage are desired, especially for display applications. The threshold voltage is the amount of voltage needed to apply across a pixel to produce a response. Addressing pixels with lower voltages allows simplification of the electronics used, resulting in the possibility for space and weight savings. The threshold voltage is inversely proportional to the dielectric anisotropy of the mixture. Therefore, one way to produce a liquid crystal mixture having a low threshold voltage is the use of mixtures having a large (positive or negative) dielectric constant.

U.S. Pat. No. 5,759,443, U.S. Pat. No. 4,873,019, CN 1928001A, and EP patent application EP0789067A1 disclose certain compounds having cyclopentyl groups.

There is a continuing need in the art for improved liquid crystal compounds and mixtures.

BRIEF SUMMARY OF THE INVENTION

Provided are liquid crystal compounds and mixtures incorporating the same. The liquid crystal compounds of the invention generally comprise a cyclopentane group and at least two other rings. In one embodiment, the liquid crystal compounds of the invention comprise a cyclopentane group and at least two other rings, one of which is a fused ring system. In one embodiment, the liquid crystal compounds of the invention comprise a terminal cyclopentane group and at least two other rings, one of which is a fused ring system. More specifically, compounds of the invention have general Formula I:

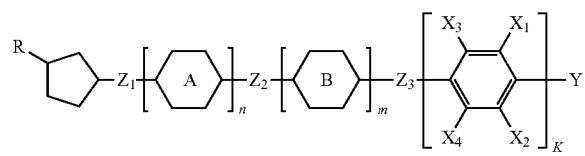

Formula I wherein
R is selected from the group consisting of H and unsubstituted or substituted alkyl each having 1-12 carbon atoms wherein the substitutions are independently one or more of halogen or —CN, wherein one or more —$CH_2$— groups of the alkyl groups may independently be replaced with —O—, —S—, —CO—, —OO—O—, —O—CO—, —O—CO—O— or —CH=CH—, provided that heteroatoms are not connected directly, except as permitted in the listed groups;

A and B are each independently selected from the group consisting of: 1,4-cyclohexylene, in which one —$CH_2$— or two not directly linked —$CH_2$— can be replaced by —O— or —S—; 1,4-cyclohexenylene; piperidine-1,4-diyl; 1,4-bicyclo[2,2,2]octylene; 1,4-phenyl; pyridin-5,2-diyl; pyrimidin-5,2-diyl; naphthalene-2,6-diyl; trans-decahydronaphthalene-2,6-diyl; tetrahydronaphthalene-2,6-diyl; indanediyl; indenediyl; phenanthrenediyl; and dibenzofurandiyl, which may each independently in each instance be substituted with one or more halogens and/or one or more $X_1$-$X_4$ substituents;

$Z_1$ is a single bond or C1-C7 unsubstituted or substituted alkylene, wherein the substitutions are independently one or more of halogen or —CN, wherein one or more —$CH_2$— groups of the alkyl groups may each independently be replaced by —O—, —S—, —CO—O—, —O—CO—, —O—CO—O— or —CH=CH— provided that heteroatoms are not connected directly to each other except as permitted in the listed groups;

$Z_2$ and $Z_3$ are each independently selected from the group consisting of: a single bond, —$(CH_2)_2$—, —$(CH_2)_4$—, —CH=$CHCH_2CH_2$—, —$CH_2CH_2$CH=CH—, —$CF_2$O—, —$OCF_2$—, —$CF_2CF_2$—, —CF=CF—, —$CH_2CF_2$—, —$CF_2CH_2$—, —$OCF_2CF_2$O—, —$C_2H_4CF_2$O—, —$CH_2CF_2OCH_2$—, —$CH_2OCF_2CH_2$—, —$OCF_2C_2H_4$—, —$C_3H_6$O—, —$OC_3H_6$—, —$C_2H_4OCH_2$—, —$CH_2OC_2H_4$—, —$CH_2$O—, —$OCH_2$—, —CH=CH—, —C≡C—, and —COO—;

n, m and K are each independently 0, 1, or 2, and m+K+n≥2;
$X_1$, $X_2$, $X_3$, and $X_4$ are each independently selected from the group consisting of: —H, —F, —Cl, —$CF_3$, —$CHF_2$, —$OCF_3$, —$OCF_2$H and —CN;

Y is independently selected from the group consisting of: —H, —F, —Cl, —CN, —NCS, —$OCHF_2$, —$CHF_2$, —$OCF_3$, —$OCF_2CF_3$, —$CF_3$, $C_{1-20}$ alkyl, $C_{1-20}$ alkoxy, $C_{1-20}$ alkenyl, and $C_{1-20}$ alkenyloxy, wherein the alkyl, alkoxy, alkenyl, and alkenyloxy groups may be independently substituted by one or more halogens;

wherein one or more hydrogen atoms in Formula I may be replaced with deuterium;

provided that when R=H and Y has less than 2 carbon atoms and $X_3$, $X_4$ are H or when R=H and Y has two or more carbon atoms and $Z_1$ has more than 3 carbon atoms, there must be a fused ring system present in the compound or one of $Z_1$, $Z_2$ and $Z_3$ must be selected from the group consisting of: C1-C3 alkylene, —CH=$CHCH_2CH_2$—, —$CH_2CH_2$CH=CH—$CF_2$O—, —$OCF_2$—, —$CF_2CF_2$—, —CF=CF—, —$CH_2CF_2$—, —$CF_2CH_2$—, —$OCF_2CF_2$O—, —$C_2H_4CF_2$O—, —CH2CF2OCH2-, —CH2OCF2CH2—, —$OCF_2C_2H_4$—, —$C_3H_6$O—, —$OC_3H_6$—, —$C_2H_4OCH_2$—, —$CH_2OC_2H_4$—, and —CH=CH—;

and provided that when R is not H and Y does not contain a —$CF_2$— group, either one of A and B is selected from the group consisting of: 1,4-cyclohexylene, in which one or two not directly linked —$CH_2$— groups can be replaced by —O— or —S—; pyridin-5,2-diyl; pyrimidin-5,2-diyl; indanediyl; indenediyl; phenanthrenediyl; and dibenzofurandiyl; or one of $Z_1$, $Z_2$ and $Z_3$ must be selected from the group consisting of: —$(CH_2)_4$—, —CH=$CHCH_2CH_2$—, —$CH_2CH_2$CH=CH—, —$CF_2$O—, —$OCF_2$—, —$CF_2CF_2$—, —CF=CF—, —$CH_2CF_2$—, —$CF_2CH_2$—, —$OCF_2CF_2$O—, —$C_2H_4CF_2$O—, —$CH_2CF_2OCH_2$—, —CH₂OCF₂CH₂—, —OCF₂C₂H₄—, —C₃H₆O—, —OC₃H₆—, —C₂H₄OCH₂—, —CH₂OC₂H₄—, —CH═CH—, and —C≡C—.

In an embodiment, $X_1$, $X_2$, $X_3$, and $X_4$ are each independently selected from the group consisting of: —H, —F, —Cl, —CF₃, —CHF₂ and —CN.

If not specified, any group, for example a ring structure, may be attached in any suitable location. If there are two or more rings linked together, for example, when n, m or k is not 0, it is noted that each of the rings may be the same of different. As an example of this, when n is 2, the two "A" rings do not need to be the same, although they may be in certain embodiments. When used herein, "indane" means:

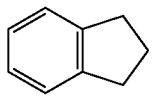

which is attached to the remainder of the structure in any suitable location(s). When used herein, "indene" means:

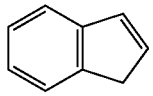

which is attached to the remainder of the structure in any suitable location(s). When linked as an A or B ring, the indane and indene groups are called indanediyl and indenediyl groups.

As used herein, a "single bond" as a variable means that there is a direct linkage between two structures. For example, if $Z_1$ is a single bond and n is 1, there is a direct linkage between the cyclopentane ring and the A ring. As used herein, a "fused ring system" has at least two rings joined together at at least two atoms. 1,4-bicyclo[2.2.2]octylene; naphthalene-2,6-diyl; decahydronaphthalene-2,6-diyl; tetrahydronaphthalene-2,6-diyl; indanediyl; indenediyl; phenanthrenediyl; and dibenzofurandiyl are all examples of fused ring systems. As used herein, halogen means fluorine, chlorine, bromine or iodine.

In one embodiment, there is at least one fused ring in a compound of the invention. In one embodiment, a compound of the invention is one of I-11 through I-17. In one embodiment, a compound of the invention is one of I-23 through I-27. In one embodiment, a compound of the invention is one of I-33 through I-35. In an embodiment, a compound of the invention is one of I-36 through I-47. In one embodiment, a compound of the invention has R═H and a fused ring system.

In an embodiment, one or more hydrogen atoms on one or more rings is replaced with deuterium. In an embodiment, one or more hydrogen atoms on a non-ring structure is replaced with deuterium.

In separate embodiments, the cyclopentene ring has one of the structures below:

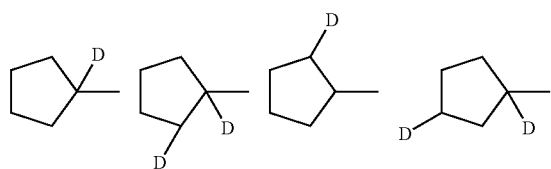

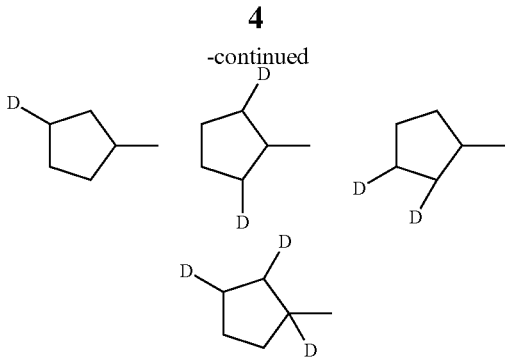

All possible locations of one or more deuterium substitution for hydrogen in the structures shown and described herein are intended to be included to the same extent as if they were individually shown.

DETAILED DESCRIPTION OF THE INVENTION

The following non-limiting description provides examples of some embodiments of the invention.

The use of one or more compounds of the invention in mixtures having desired properties for various liquid crystal applications is known to one of ordinary skill in the art without undue experimentation.

Devices comprising one or more compounds of the invention can be made and operated by one of ordinary skill in the art without undue experimentation.

The description herein provides some additional exemplary embodiments of the invention and variables which can be separate or combined together in all possible permutations, independently and in combination, to formulate compounds of the invention.

The compounds of the invention have a high dielectric constant which may be positive or negative. The use of compounds and mixtures having negative or positive dielectric constants is known in the art. In some embodiments of the invention, the compounds have positive dielectric constant of at least 8. In some embodiments of the invention, the compounds have a negative dielectric constant of −2 or less. Larger positive and larger negative numbers are desired.

Positive Dielectric Constant Compounds

Specific particular embodiments of compounds of the invention having positive dielectric constants are shown below in structures I-1 through I-17, where the variables have the following definitions:

Y is independently selected from the group consisting of —F, —Cl, —CF₃, —OCF₃, —OCHF₂, —OCF₂CF₃, —OCF═CF₂, —OCHFCF₃, —OCF₂CF═CF₂;

$X_1$, $X_2$, $X_3$, $X_4$ are each, independently of one another, —H or —F;

Z is independently selected from the group consisting of: single bond, —C₂H₄—, —CF₂O—, —CF═CF—, —C₂F₄—, —CO₂—, —C₄H₈—, —C₂H₄CF₂O—, —OCF₂CF₂O—, —CH═CHCH₂CH₂—, —CH₂CH₂CH═CH—; and R is C1-C12 alkyl or H.

I-1

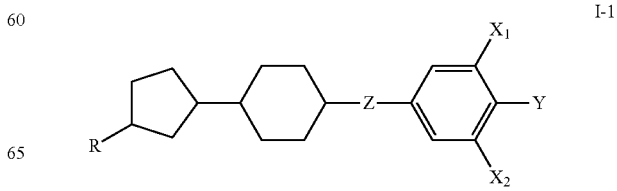

-continued
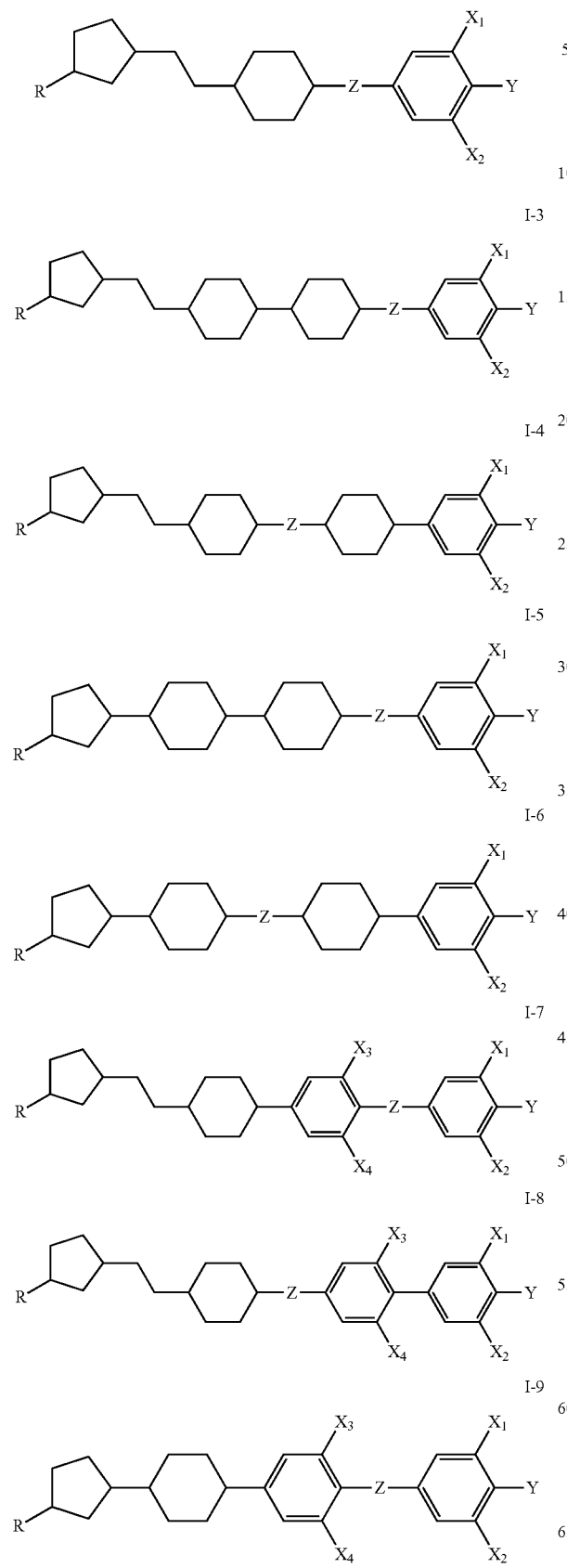
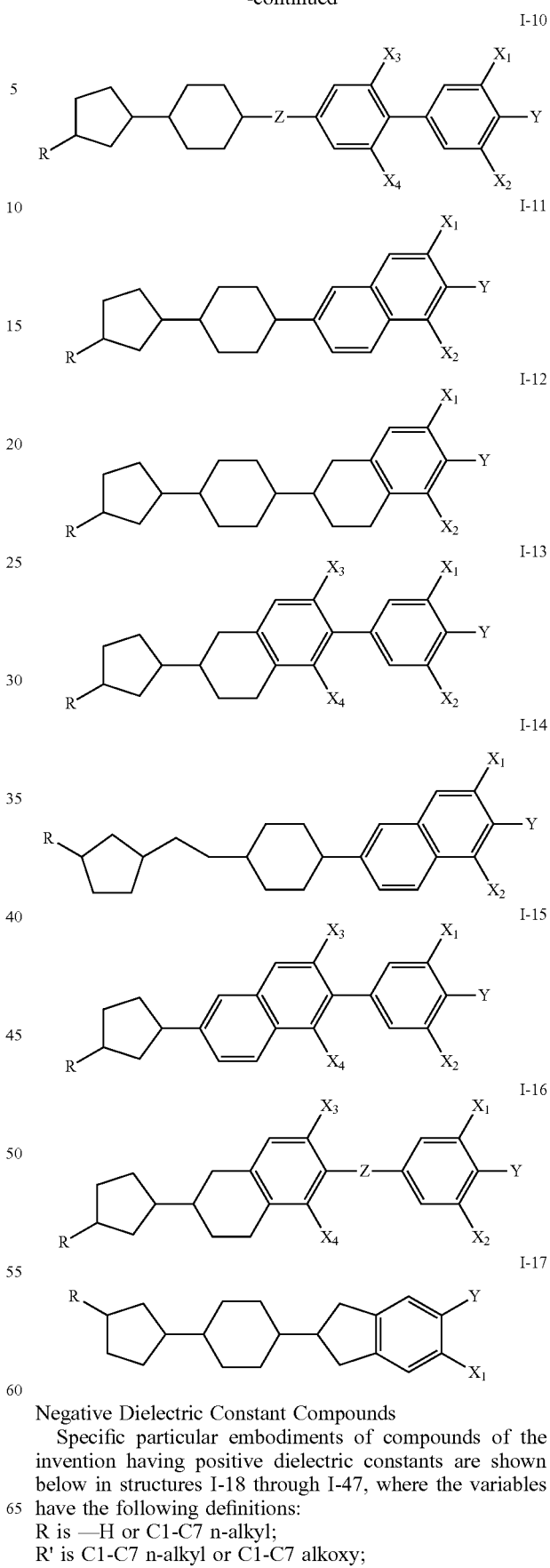
Negative Dielectric Constant Compounds
Specific particular embodiments of compounds of the invention having positive dielectric constants are shown below in structures I-18 through I-47, where the variables have the following definitions:
R is —H or C1-C7 n-alkyl;
R' is C1-C7 n-alkyl or C1-C7 alkoxy;

$X_1$ and $X_2$ are each independently selected from the group consisting of —F, —Cl, —CF$_3$, —CHF$_2$, —OCF$_3$ and —OCF$_2$H;
$X_3$, $X_4$, $X_5$ and $X_6$ are each independently —H or —F;
Z is independently single bond, —C$_2$H$_4$—, —C$_4$H$_8$—, —CF$_2$O—, —CF=CF—, —C$_2$F$_4$—, —C$_2$H$_4$CF$_2$O— or —CO$_2$—.
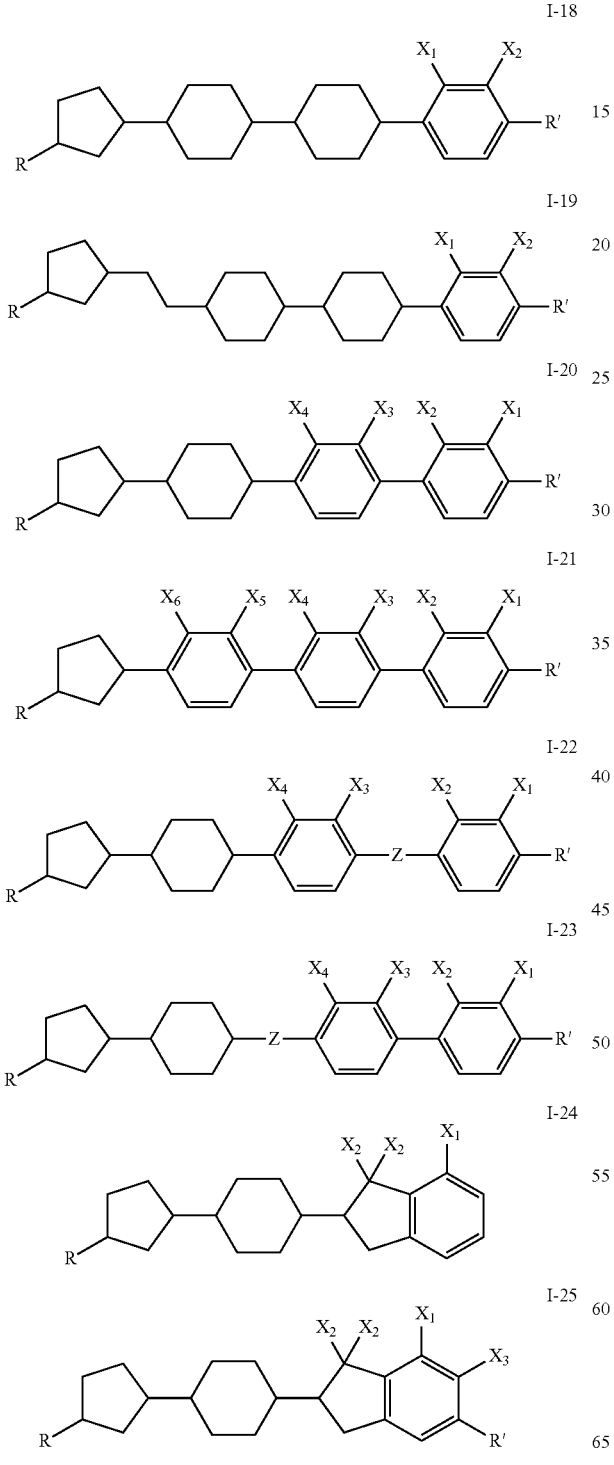
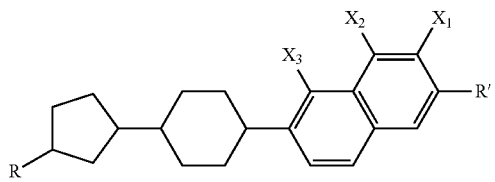
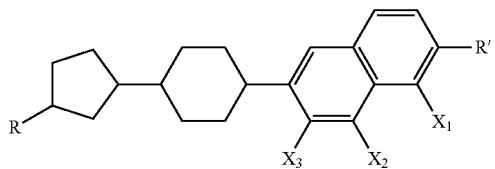
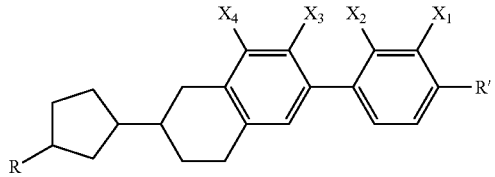
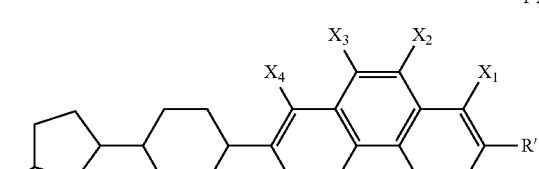
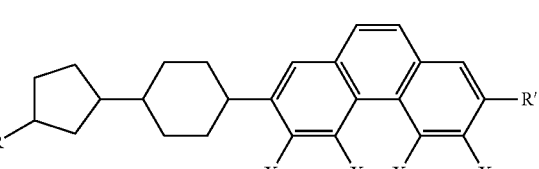
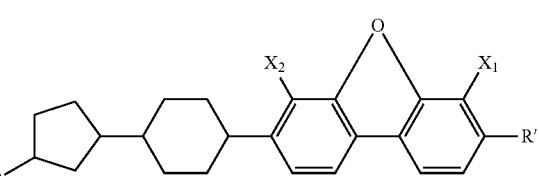
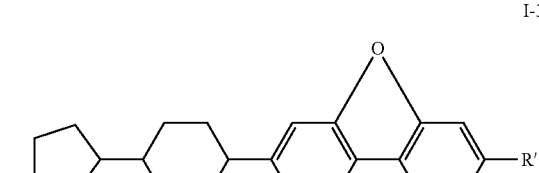
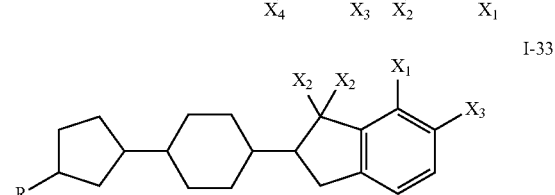

-continued

I-34
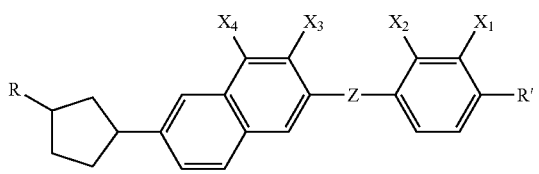

I-35
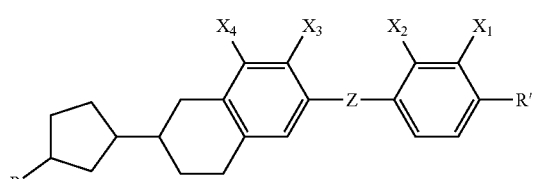

I-36
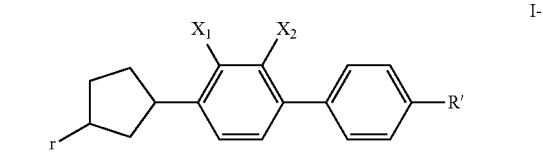

I-37
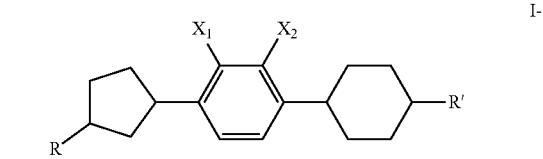

I-38
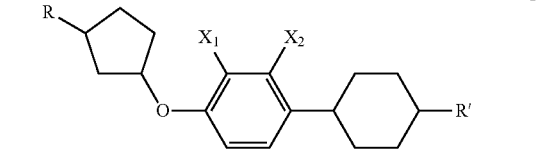

I-39
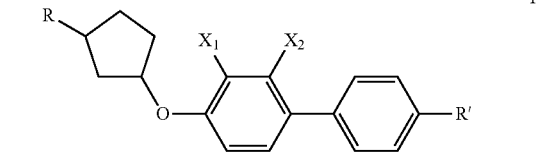

I-40
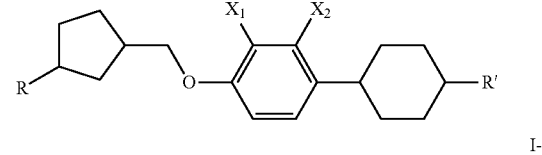

I-41
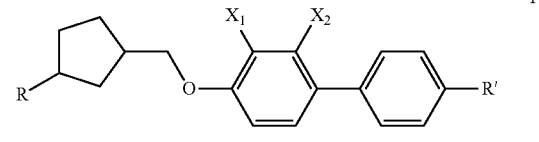

I-42
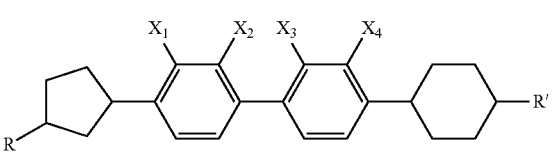

-continued

I-43
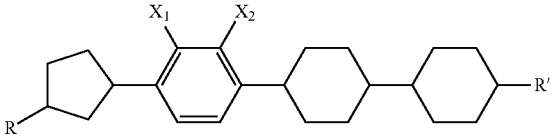

I-44
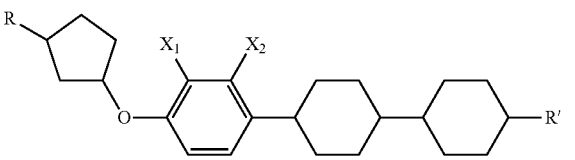

I-45
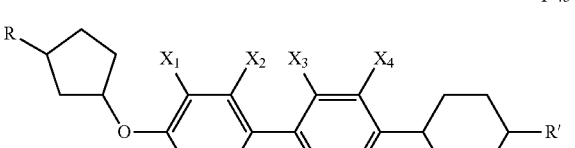

I-46
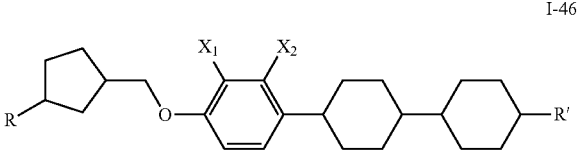

I-47
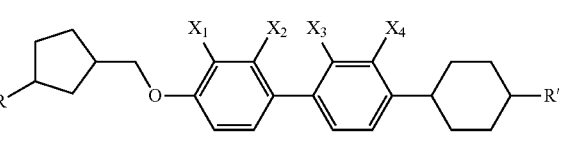

Mixtures

As known in the art, there are typically many components of liquid crystal mixtures, as determined by the desired use of the mixture. The composition of the liquid crystal mixtures of the invention can be determined by one having ordinary skill in the art without undue experimentation. The addition of one or more compounds of the invention in liquid crystal mixtures improves the properties of the mixture, including lowering threshold voltage, increasing switching speed and other properties which are known in the art.

Positive Dielectric Constant Mixture

The compounds of the invention may be used as components in any desired liquid crystal mixture, such as those mixtures known in the art. In one embodiment, the liquid crystal mixture comprises one or more compounds of Formula I. In one embodiment, the liquid crystal mixture has positive dielectric constant. In one embodiment, the liquid crystal mixture having positive dielectric constant comprises one or more compounds of Formula I-1 through I-17.

The mixture may include one or more compounds of Formula I and one or more compounds of Formula II-XVI:

II
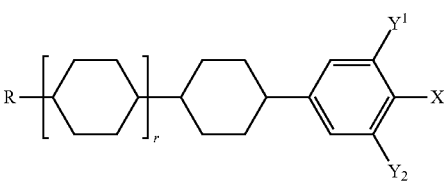

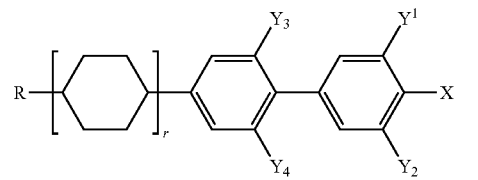
III

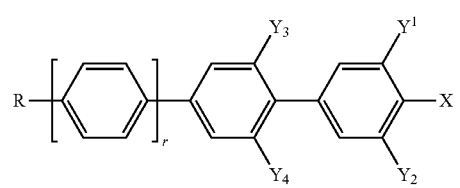
IV

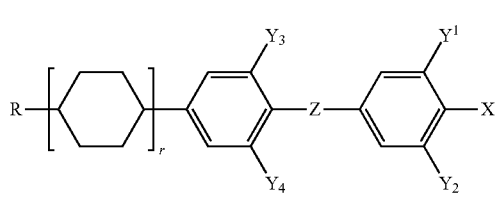
V

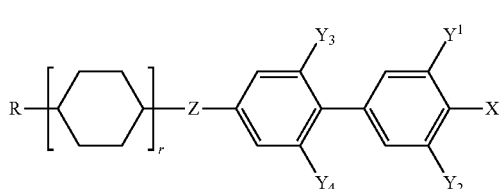
VI

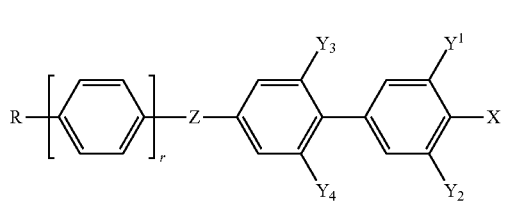
VII

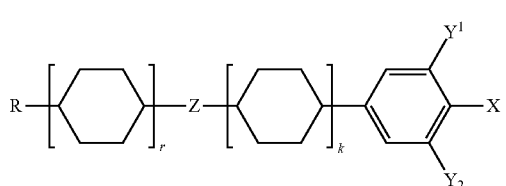
VIII

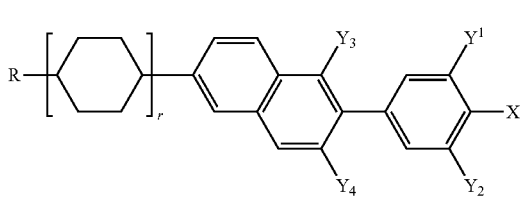
IX

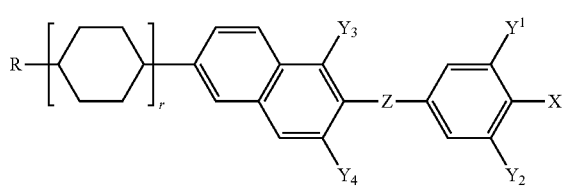
X

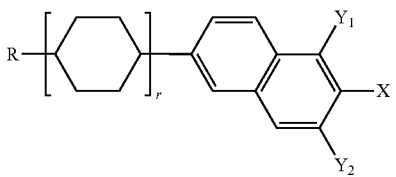
XI

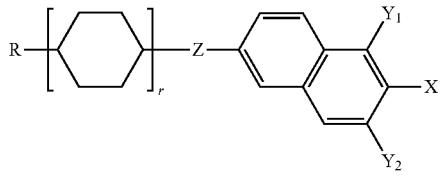
XII

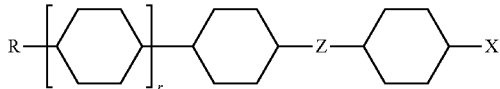
XIII

XIV

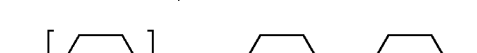
XV

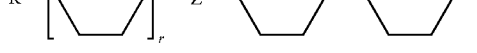
XVI in which the individual variables have the following definitions:

R is C1-C9 n-alkyl, C1-C9 alkoxy, C1-C9 oxaalkyl, C1-C9 fluoroalkyl or C1-C9 alkenyl;

X is —F, —Cl, halogenated C1-C6 alkyl, halogenated C1-C6 alkenyl, halogenated C1-C6 alkenyloxy or halogenated C1-C6 alkoxy;

Z is —$C_2H_4$—, —$C_4H_8$—, —CH=CH—, —$CH_2O$—, —COO—, —$OCH_2$—, —$OCF_2$—, —$CF_2O$—, —CF=CF—, —$C_2H_4$—, —$CH_2CF_2$— or —$CF_2CH_2$—;

$Y_1$, $Y_2$, $Y_3$ and $Y_4$ are each, independently of one another, —H or —F; and r is 0, 1 or 2; and k is 0 or 1, provided that if both r and k appear in the same formula, r+k≥2.

Additional specific examples of compounds which may be included in a mixture are shown below where R is as defined for compounds II-XVI:

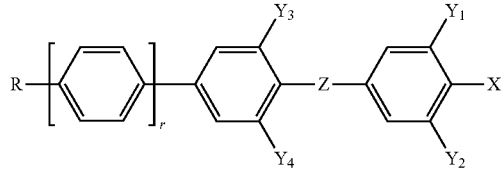

-continued
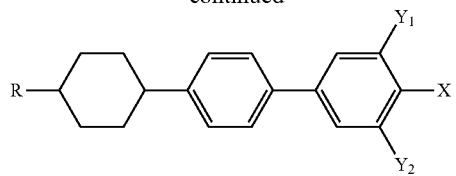
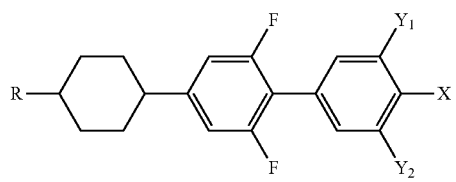
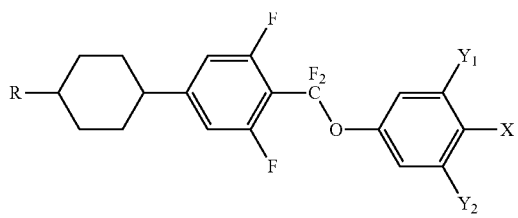
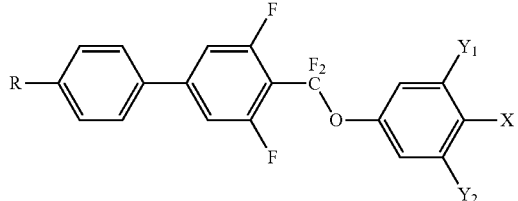
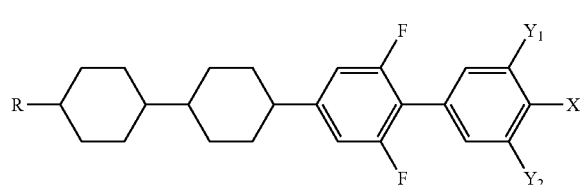
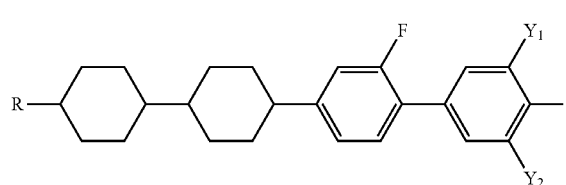
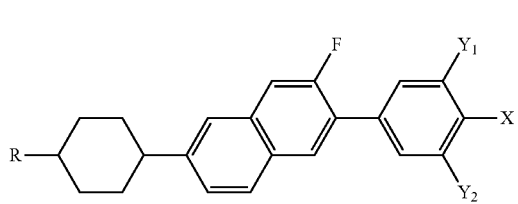
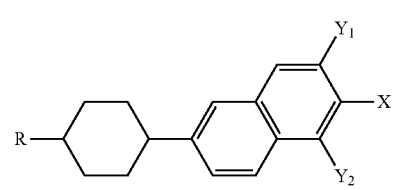
In each of the formulas shown herein, the structure:
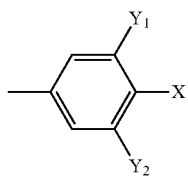
may have any of the following formulas:
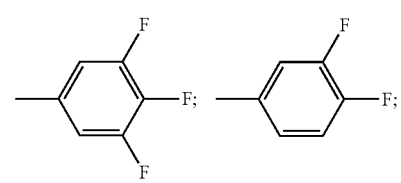
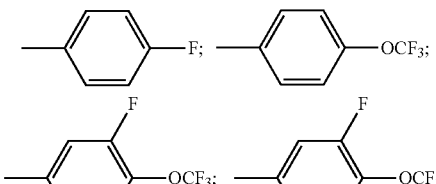
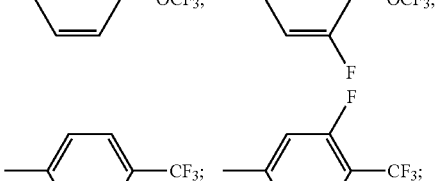
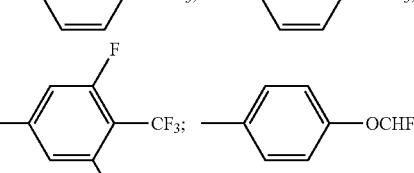
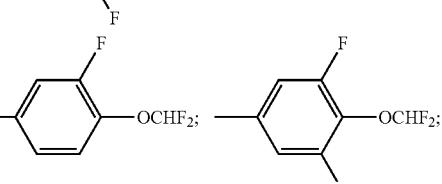
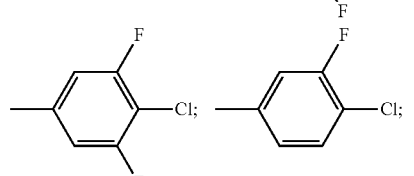
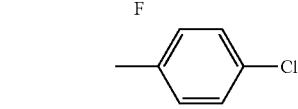
In other embodiments, the mixture may comprise one or more compounds of Formula I and one or more compounds selected from the group consisting of compounds of the structure below XVII-XXIII.

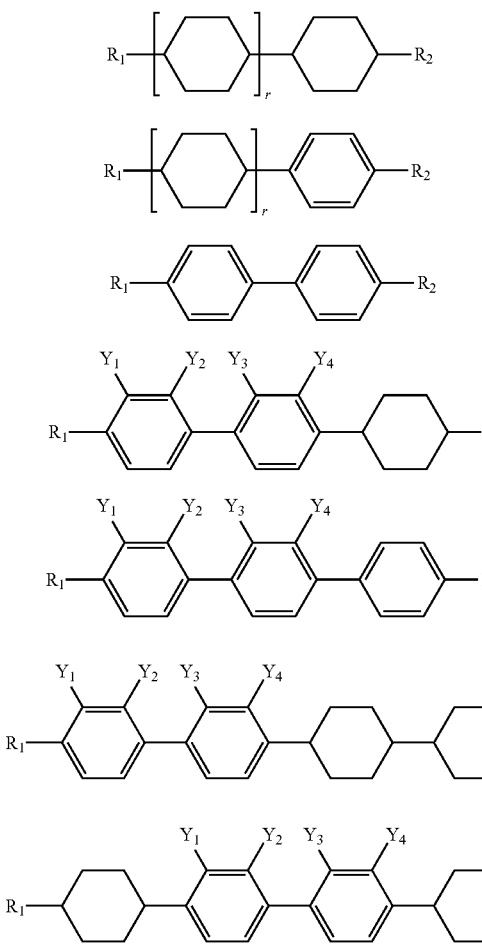

XVII

XVIII

XIX

XX

XXI

XXII

XXIII where the variables have the following definitions:
$R_1$ and $R_2$ are each independently C1-C9 n-alkyl, C1-C9 alkoxy, C1-C9 oxaalkyl, or C1-C9 alkenyl;
$Y_1$, $Y_2$, $Y_3$ and $Y_4$ are each, independently of one another, —H or —F, and
r is 0, 1 or 2.

Negative Dielectric Constant Mixtures

In one embodiment, the liquid crystal mixture has negative dielectric constant. In one embodiment, the liquid crystal mixture having negative dielectric constant comprises one or more compound of Formula I-18 through I-47. In another embodiment, the liquid crystal mixture having negative dielectric constant comprises one or more compounds of Formula I, such as 1-18 to 1-47 and additionally comprises a useful amount of one or more compounds selected from the group consisting of compounds of the general formulae XXIV to XLIV, where the variables are as defined below:
R is C1-C8 n-alkyl, C1-C8 alkoxy, C1-C8 alkenyl or C1-C8 alkenyloxy;
R' is C1-C8 alkyl, C1-C8 alkoxy, C1-C8 alkenyl or C1-C8 alkenyloxy;
$X_1$, $X_2$, $X_3$, $X_4$, $X_5$ and $X_6$ are independently selected from the group consisting of: —H, —F, —Cl, —CHF$_2$, —CF$_3$, —OCF$_3$ and —OCHF$_2$; with the proviso that at least two from $X_1$ to $X_6$ are —F, —Cl, —CHF$_2$ or —CF$_3$;
Z is independently selected from the group consisting of: single bond, —C$_2$H$_4$—, —C$_4$H$_8$—, —CH=CHCH$_2$CH$_2$—, —CH$_2$CH$_2$CH=CH—, —CF$_2$O—, —OCF$_2$—, —CF=CF—, —C$_2$F$_4$—, —C$_2$H$_4$CF$_2$O—, —OCF$_2$C$_2$H$_4$— and —CO$_2$—;
r is 0, 1 or 2; k is 0 or 1, providing that r+k≥2.

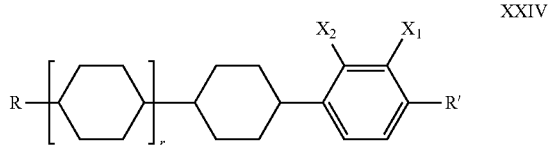

XXIV

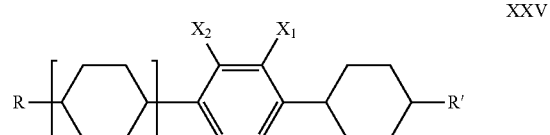

XXV

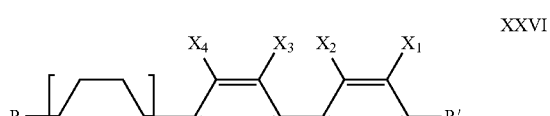

XXVI

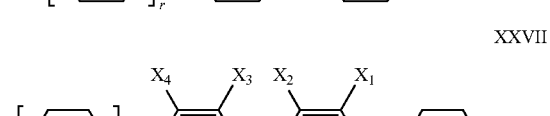

XXVII

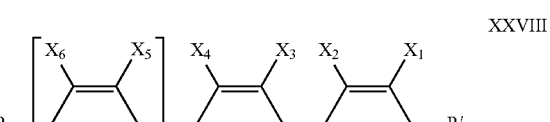

XXVIII

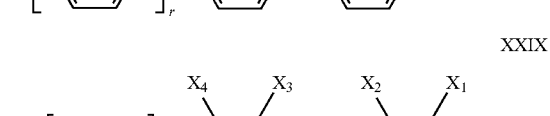

XXIX

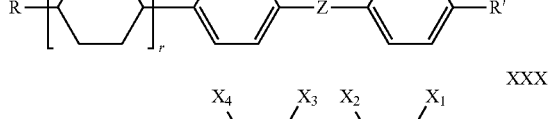

XXX

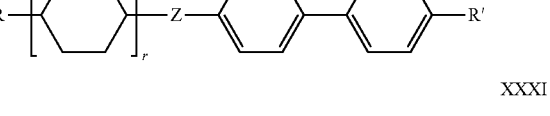

XXXI

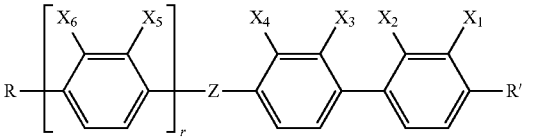

XXXII

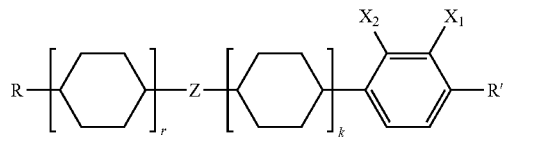

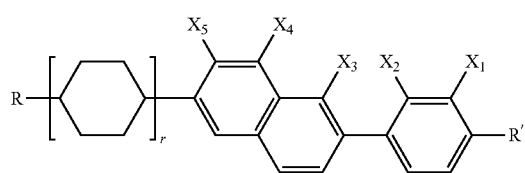

XXXIII

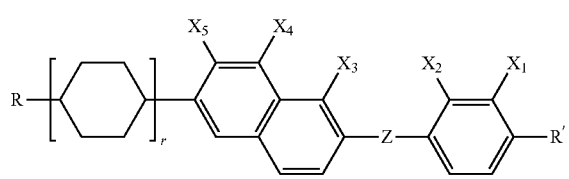

XXXIV

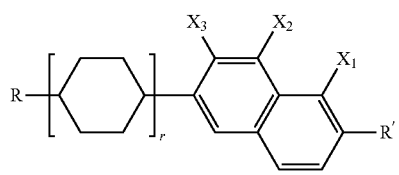

XXXV

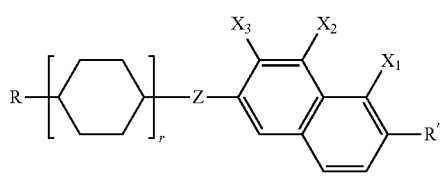

XXXVI

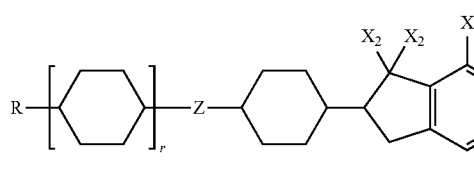

XXXVII

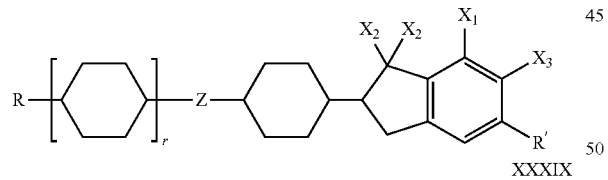

XXXVIII

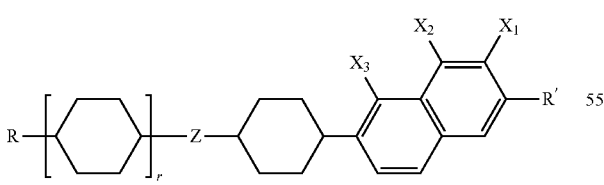

XXXIX

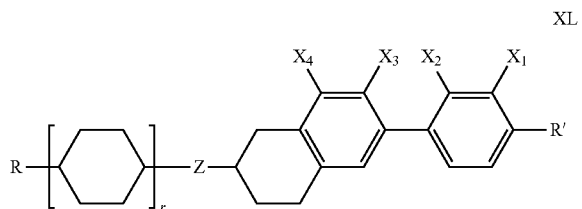

XL

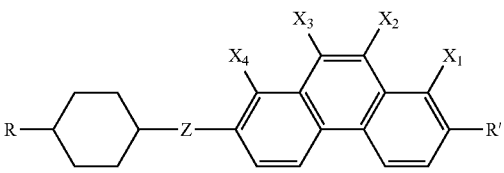

XLI

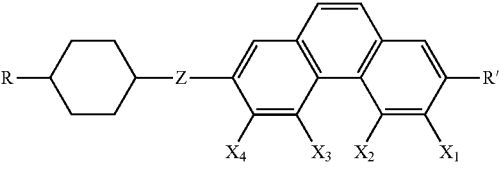

XLII

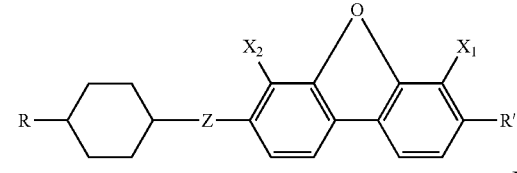

XLIII

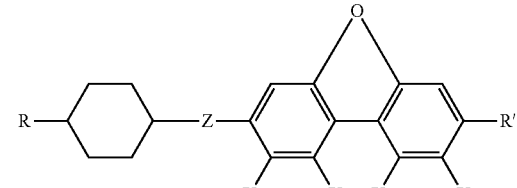

XLIV

In other specific embodiments, the negative dielectric constant mixture may comprise one or more compounds of Formula I and one or more compounds selected from the group consisting of compounds of formulas XLV-XLVIII below.

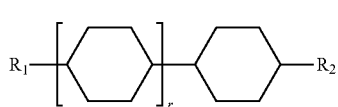

XLV

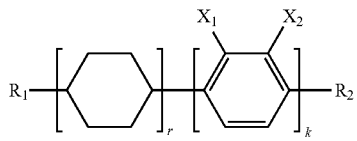

XLVI

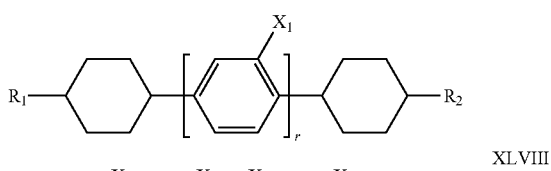

XLVII

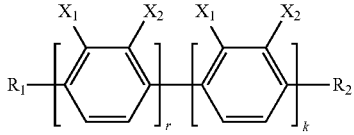

XLVIII in which the individual variables have the following definitions:

$R_1$ and $R_2$ are each independently C1-C8 n-alkyl, C1-C8 alkoxy, C1-C8 oxaalkyl, C1-C8 alkenyl, or C1-C8 alkenyloxy;

$X_1$, $X_2$, $X_3$, and $X_4$ are —H or —F, provided that only one of $X_1$, $X_2$, $X_3$, and $X_4$ may be F in the same compound;
r is 1 or 2; k is 1 or 2.

The compounds of the invention may be used in any useful amount in a liquid crystal mixture, including less than 0.1% by weight of the total composition; less than 0.5% by weight of the total composition; less than 1% by weight of the total composition, less than 3% by weight of the total composition; less than 5% by weight of the total composition; less than 7% by weight of the total composition; less than 10% by weight of the total composition; less than 20% by weight of the total composition; less than 25% by weight of the total composition; less than 30% by weight of the total composition; less than 35% by weight of the total composition; less than 40% by weight of the total composition; less than 50% by weight of the total composition; and any other useful amount.

In one embodiment, there is between 0.5% and 80% of one or more compounds of Formula I. In one embodiment, there is between 0.5% and 80% of one or more compounds of Formula I-1 through I-17. In one embodiment, there is between 0.5% and 80% of one or more compounds of Formula I-18 through I-35. In one embodiment, there is between 0.5% and 80% of one or more compounds of Formula I, and between 0.5% and 80% or one or more compounds of a compound of formula II-XVI In one embodiment, there is between 0.5% and 80% of one or more compounds of Formula I, and between 0.5% and 80% of one or more compounds of Formula XVII-XXIII. In one embodiment, there is between 0.5% and 80% of one or more compounds of Formula I, between 0.5% and 80% or one or more compounds of Formula II-XVI, and between 0.5% and 80% of one or more compounds of Formula XVII-XXIII. In one embodiment, there is between 0.5% and 80% of one or more compounds of Formula I, and between 0.5% and 80% or one or more compounds of a compound of formula XXIV-XLIV. In one embodiment, there is between 0.5% and 80% of one or more compounds of Formula I, and between 0.5% and 80% of one or more compounds of Formula XLV-XLVIII. In one embodiment, there is between 0.5% and 80% of one or more compounds of Formula I, between 0.5% and 80% or one or more compounds of Formula XXIV-XLIV, and between 0.5% and 80% of one or more compounds of Formula XLV-XLVIII. There may be other components, as known in the art.

Synthesis

The following describes exemplary synthesis reactions for compounds of the invention. Conditions for such as reaction are well-known to one of ordinary skill in the art. The synthesis of compounds of the invention not specifically exemplified here can be carried out by one of ordinary skill in the art without undue experimentation using methods known in the art.

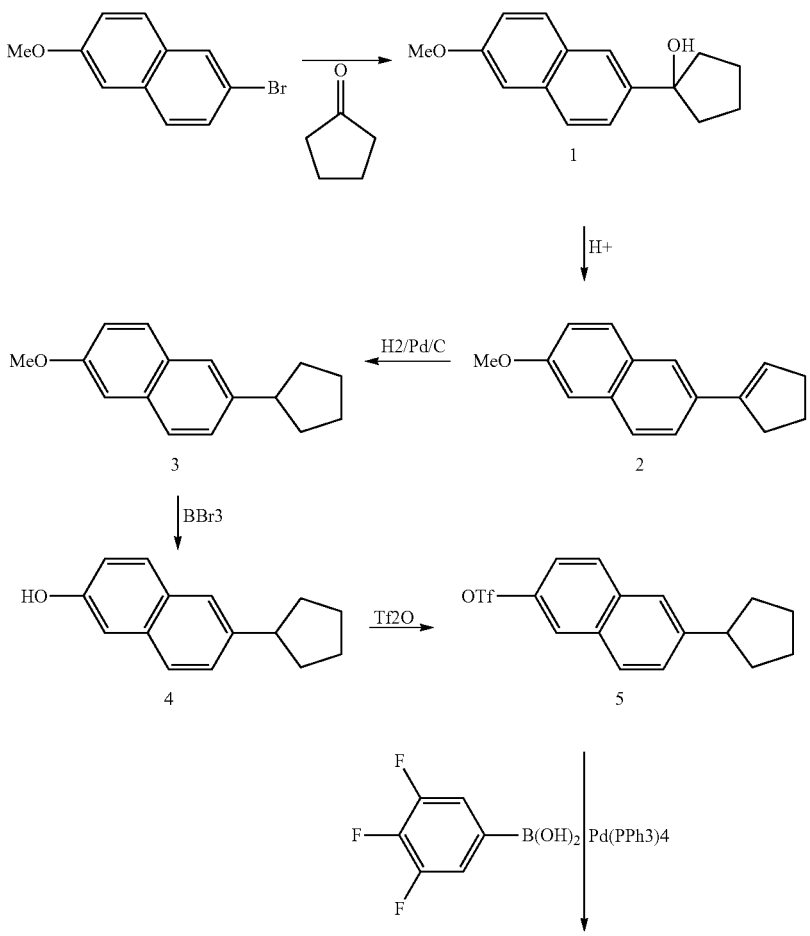

Scheme 1

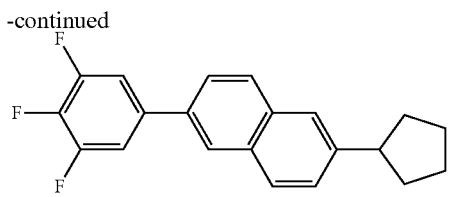

6

EXPERIMENTAL

Synthesis of 2-Cyclopentyl-6-(3,4,5-trifluorophenyl)naphthalene

Synthesis of 1-(6-methoxynaphthalene-2-yl)cyclopentanol (Compound 1)

Grignard reagent was prepared from 6-methoxy-2-bromonaphthalene, dry Mg, a crystal of iodine and a drop of 1,2-dibromoethane in dry THF. This mixture was then cooled in an ice-sodium chloride bath, a solution of dried cyclopentanone dry THF was added drop wise via syringe. The resultant reaction mixture was then slowly warmed to room temperature. Then refluxed for additional 10 hours and cooled to room temperature, added to ice cold HCl and extracted using ethyl acetate. The combined organic extracts were washed with sat. $NH_4Cl$ solution and dried over $MgSO_4$. The crude product obtained was passed through a column of silicagel using 15% EA in hexane as eluent. Yield of the product: 70%.

2-Cyclopentenyl-6-methoxynaphthalene (Compound 2)

A solution of compound 1 in dry benzene, and a catalytic amount (2 wt %) of p-toluene-sulfonic acid were placed in a round-bottomed flask. The resulting solution was then heated at 50° C. for 15 minutes, the reaction was complete, and the resulting solution was cooled to room temperature, passed through a short pad of silicagel. Yield was almost quantitative, the product obtained was pure enough which was directly used for the next reaction.

2-Cyclopentyl-6-methoxynaphthalene (Compound 3)

To a solution of compound 2 in ethyl acetate was added a catalytic amount (5 wt %) of 5% Pd—C, the resulting solution was continued stirring vigorously until the reaction is complete. Yield was almost quantitative. The product obtained was pure enough, which was directly used for the next reaction.

6-Cyclopentylnaphthalen-2-ol (Compound 4)

A solution of compound 3 in dry dicloromethane was cooled to −78° C. in dry ice and acetone under argon. To this with stirring, a solution of $BBr_3$ in dicloromethane was added dropwise and the resulting solution was continued stirring for additional 2 hours at this temperature and allowed to warm to room temperature overnight. The resultant solution was extracted using ethyl acetate, the crude product was crystallized from a mixture of methanol and hexane. Yield: 92%.

6-Cyclopentylnaphthalen-2-yl trifluoromethylsulfonate (Compound 5)

A solution of compound 4 and pyridine in dry dichloromethane was cooled to 5° C. using ice bath. To this with stirring, a solution of triflic anhydride in dichloromethane was added dropwise which was allowed to warm to room temperature, and continued stirring for additional 2 hours. The resultant solution was extracted using ethyl acetate, the product obtained was a low melting solid, which was directly used for the next step. Yield: 95%.

2-Cyclopentyl-6-(3,4,5-trifluorophenyl) naphthalene (Compound 6)

Into a flame dried 100 ml round-bottomed flask with a magnetic stir bar, was charged with compound 5 (1.0 g, 2.9 mMol), 3,4,5-trifluorophenyl boronic acid (0.56 g, 3.19 mMol), 20 mL toluene, 2M $K_2CO_3$ (20 mL), $Bu_4NBr$ (25 mg) and the mixture flushed with argon for 10 min. [Pd $(PPh_3)_4$] (0.1 g) was added and the mixture heated under argon at −85° C. for 12 h, with vigorous stirring. After cooling to room temperature, 25 mL water was added, extracted with 3×10 mL ethyl acetate, the organic extracts dried over $MgSO_4$, and the crude product was then passed through a column of silica gel using hexane as eluent, also crystallized from hexane. Yield, 0.89 g (94%).

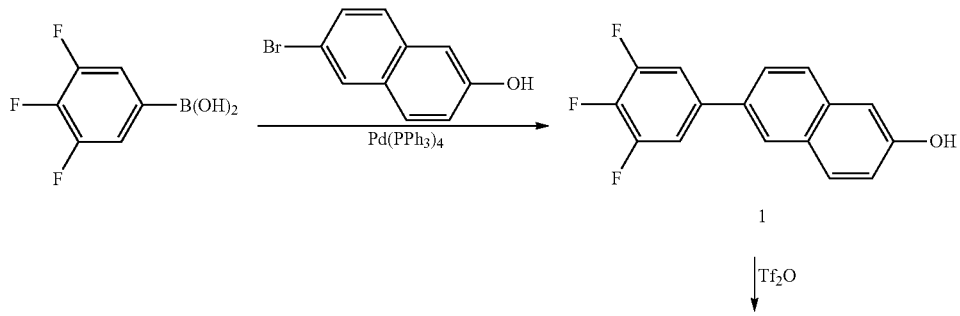

Scheme 2

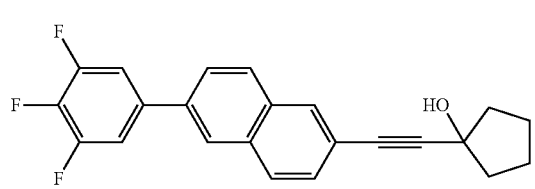

3

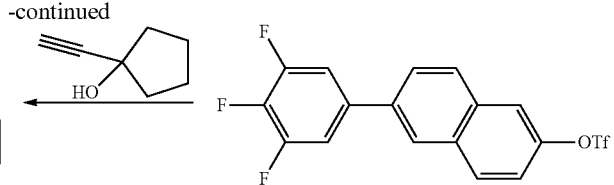

2

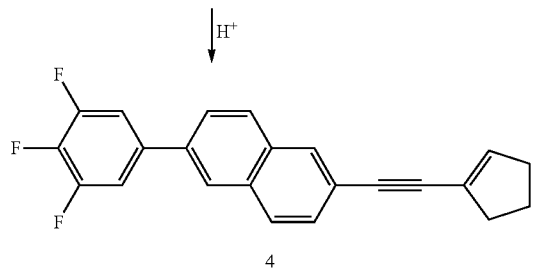

4

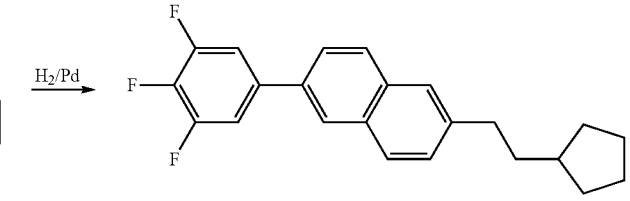

5

Synthesis of 2-(Cyclopentylethyl)-6-(3,4,5-trifluorophenyl)naphthalene 1. 6-(3,4,5-trifluorophenyl) naphthalene-2-ol (Compound 1)

A flame dried 500 ml round-bottomed flask with a magnetic stir bar, was charged with 6-hydroxy-2-bromonaphthalene (8.0 g, 35.89 mMol), 3,4,5-trifluorophenyl boronic acid (6.9 g, 39.5 mMol), 75 mL toluene, 2M $K_2CO_3$ (80 mL), $Bu_4NBr$ (50 mg) and the mixture flushed with argon for 10 min. [$Pd(PPh_3)_4$] (0.5 g) was added and the mixture heated under argon at ~85° C. overnight, with vigorous stirring. After cooling to room temperature, 50 mL water was added, extracted with 3×25 mL ethyl acetate, the organic extracts dried over $MgSO_4$, and the crude product was then crystallized from a mixture of hexane and few drops of methanol. Yield: 8 g (87%).

6-(3,4,5-trifluorophenyl)naphthalene-2-yl trifluoromethylsulfonate (Compound 2)

A solution of compound 1 and pyridine in dry dichloromethane was cooled to 5 C using ice bath. To this with stirring, a solution of triflic anhydride in dichloromethane was added drop wise which is allowed to warm to room temperature, and continued stirring for additional 2 hours. The resultant solution was extracted using ethyl acetate, the product obtained was crystallized from dichloromethane and hexane mixture. Yield: 90%.

1-((6-(3,4,5-trifluorophenyl)naphthalen-2-yl)ethynyl)cyclopentanol (Compound 3)

To a solution of triflet (compound 2) and 1-ethynylcyclopentanol in dry DMF under argon, $Pd(PPh_3)_4$, CuI and triethylamine were successively added, and the reaction mixture was stirred overnight at room temperature. The mixture was then diluted with EtOAc, washed with water and dried over MgSO4. Yield: 93%.

2-(Cyclopentylethynyl)-6-(3,4,5-trifluorophenyl) naphthalene (Compound 4)

A solution of compound 3 in dry benzene, and a catalytic amount (2 wt %) of p-toluene-sulfonic acid were placed in a round-bottomed flask. The resulting solution is then heated at 50 C for 3-4 hours, the reaction was complete, and the resulting solution was cooled to room temperature, and passed through a short pad of silicagel. The product obtained was crystallized from a mixture of hexane and dichloromethane. Yield: 90%.

5. 2-(Cyclopentylethyl)-6-(3,4,5-trifluorophenyl) naphthalene (Compound 5)

To a solution of compound 4 in ethyl acetate was added a catalytic amount (5 wt %) of 5% Pd—C, the resulting solution was continued stirring vigorously until the reaction was complete. The product obtained was crystallized from hexane. Yield 92%.

Incorporation of Deuterium into Structures:

Methods of incorporating one or more deuterium atoms into a structure are known in the art.

Characterization methods and property analysis of compounds and mixtures are well-known in the art. Methods to alter the material properties of a mixture, such as adding other compound to a mixture, or by adding more or less of a compound in a mixture, are also known in the art.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim and are intended to be able to be removed individually or collectively.

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, synthetic methods, and mixture constituents other than those specifically exemplified can be employed in the practice of the invention without resort to undue experimentation. All art-known functional equivalents, of any such methods, device elements, starting materials, synthetic methods, and mixture constituents are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The definitions are provided to clarify their specific use in the context of the invention.

One skilled in the art would readily appreciate that the present invention is well adapted to carry out the objects and obtain the ends and advantages mentioned, as well as those inherent therein. The liquid crystal compounds and methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

Although the description herein contains many specificities, these should not be construed as limiting the scope of the invention, but as merely providing illustrations of some of the embodiments of the invention. Thus, additional embodiments are within the scope of the invention and within the claims. All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

We claim:

1. A compound having the formula:

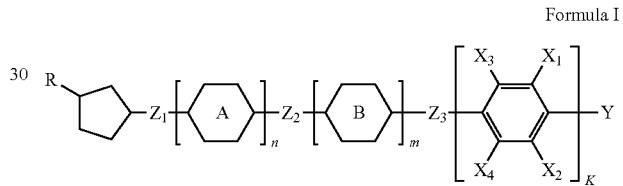

Formula I wherein

R is selected from the group consisting of H and unsubstituted or substituted alkyl each having 1-12 carbon atoms wherein the substitutions are independently one or more of halogen or CN, wherein one or more —$CH_2$— groups of the alkyl groups are optionally independently replaced with —O—, —S—, —CO—, —CO—O—, —O—CO—, —O—CO—O— or —CH=CH—, provided that heteroatoms are not connected directly, except as permitted in the listed groups;

A and B are each independently selected from the group consisting of: 1,4-cyclohexyl, in which one —$CH_2$— or two not directly linked —$CH_2$— are optionally replaced by O or S; 1,4-cyclohexenyl; piperidine-1,4-diyl; 1,4-bicyclo[2,2,2]octylene; 1,4-phenyl, which are optionally substituted with one or more halogens; Pyridin-5,2-diyl; pyrimidin-5,2-diyl; naphthalene-2,6-diyl; trans-decahydronaphthalene-2,6-diyl; tetrahydronaphthalene-2,6-diyl; indane; indene; phenanthryl; and dibenzofuran, which are optionally independently in each instance substituted with one or more halogens and/or one or more $X_1$-$X_4$ substitutents;

$Z_1$ is a single bond or C1-7 unsubstituted or substituted alkylene, wherein the substitutions are independently one or more of halogen or CN, wherein one or more —$CH_2$— groups of the alkyl groups are optionally independently replaced by —O—, —S—, —CO—O—, —O—CO—, —O—CO—O— or —CH=CH— provided that heteroatoms are not connected directly to each other except as permitted in the listed groups;

$Z_2$ and $Z_3$ are each independently selected from the group consisting of: a single bond, —$(CH_2)_2$—, —$(CH_2)_4$—, —CH=CHCH₂CH₂—, —CH₂CH₂CH=CH—, —CF₂O—, —OCF₂—, —CF₂CF₂—, —CF=CF—, —CH₂CF₂—, —CF₂CH₂—, —OCF₂CF₂O—, —C₂H₄CF₂O—, —CH₂CF₂OCH₂—, —CH₂OCF₂CH₂—, —OCF₂C₂H₄—, —C₃H₆O—, —OC₃H₆—, —C₂H₄OCH₂—, —CH₂OC₂H₄—, —CH₂O—, —OCH₂—, —CH=CH—, —C≡C—, and —COO—;

n, m and K are each independently 0, 1, or 2, and m+K+n≥2;

X₁, X₂, X₃, and X₄ are each independently selected from the group consisting of: H, F, Cl, CF₃, CHF₂, OCF₃, OCF₂H and CN;

Y is independently selected from the group consisting of: —H, —F, —CN, —NCS, —OCHF₂, —CHF₂, —OCF₃, —OCF₂CF₃, —CF₃, C₁₋₂₀ alkyl, C₁₋₂₀ alkoxy, C₁₋₂₀ alkenyl, and C₁₋₂₀ alkenyloxy, wherein the alkyl, alkoxy, alkenyl, and alkenyloxy groups are optionally independently substituted by one or more halogens;

wherein one or more hydrogen atoms in Formula I are optionally replaced with deuterium;

provided that when R=H and Y has less than 2 carbon atoms and X₃, X₄ are H or when R=H and Y has two or more carbon atoms and Z₁ has more than 3 carbon atoms, there must be a fused ring system present in the compound or one of Z₁, Z₂ and Z₃ must be selected from the group consisting of: C1-C3 alkylene, —CH=CHCH₂CH₂—, —CH₂CH₂CH=CH—, —CF₂O—, —OCF₂—CF₂CF₂—, —CF=CF—, —CH₂CF₂—, —CF₂CH₂—, —OCF₂CF₂O—, —C₂H₄CF₂O—, —CH₂CF₂OCH₂—, —CH₂OCF₂CH₂—, —OCF₂C₂H₄—, —C₃H₆O—, —OC₃H₆—, —C₂H₄OCH₂—, —CH₂OC₂H₄—, and —CH=CH—;

and provided that when R is not H and Y does not contain a —CF₂— group, either one of A and B is selected from the group consisting of: 1,4-cyclohexene, in which one or two not directly linked —CH₂— groups are optionally replaced by —O— or —S—; Pyridin-5,2-diyl; pyrimidin-5,2-diyl; indane; indene; phenanthryl, and dibenzofuran; or one of Z₁, Z₂ and Z₃ must be selected from the group consisting of: —(CH₂)₄—, —CH=CHCH₂CH₂—, —CH₂CH₂CH=CH—, —CF₂O—, —OCF₂—, —CF₂CF₂—, —CF=CF—, —CH₂CF₂—, —CF₂CH₂—, —OCF₂CF₂O—, —C₂H₄CF₂O—, —CH2CF₂OCH₂—, —CH₂OCF₂CH₂—, —OCF₂C₂H₄—, —C₃H₆O—, —OC₃H₆—, —C₂H₄OCH₂—, —CH₂OC₂H₄—, —CH=CH—, and —C≡C—.

2. The compound of claim 1 having a positive dielectric constant.

3. The compound of claim 1 having a negative dielectric constant.

4. A liquid crystal mixture having positive dielectric constant comprising a compound of claim 1.

5. The mixture of claim 4, wherein the mixture further comprises at least one compound of formula II-XVI:

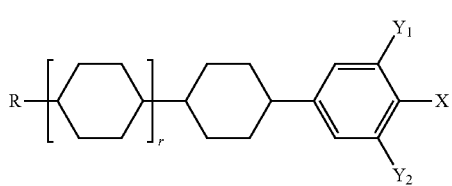

II

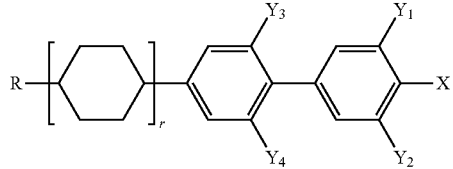

III

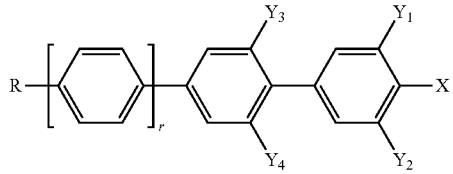

IV

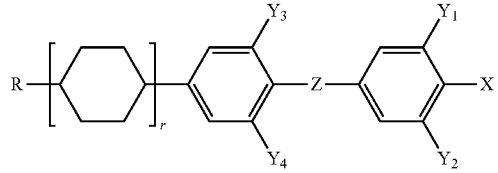

V

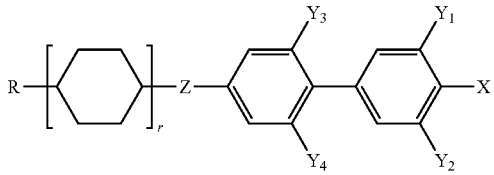

VI

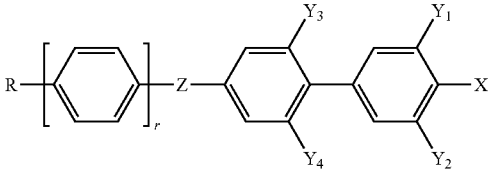

VII

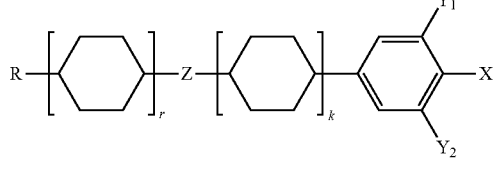

VIII

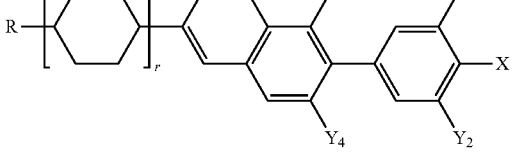

IX

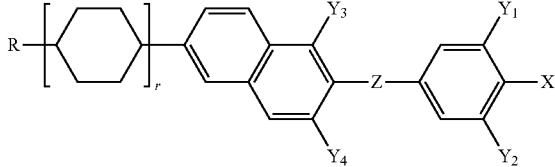

X

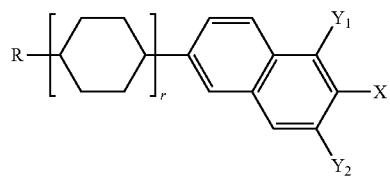
XI
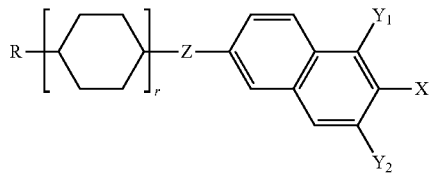
XII
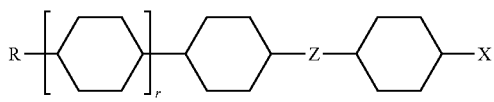
XIII
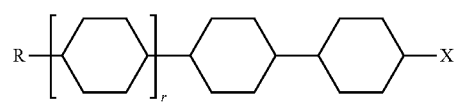
XIV
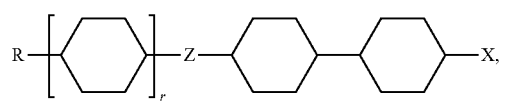
XV
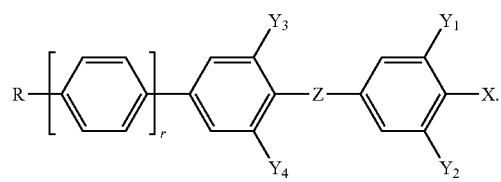
XVI
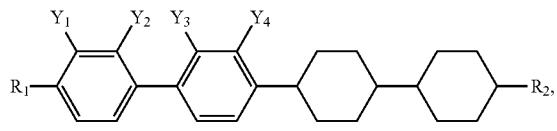
XXII
or
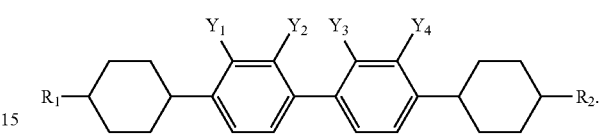
XXIII
7. The mixture of claim 4, wherein the mixture comprises at least one compound of formula II-XVI and at least one compound of formula XVII-XXIII wherein:
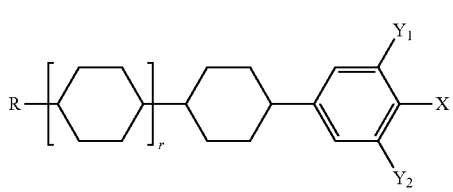
II
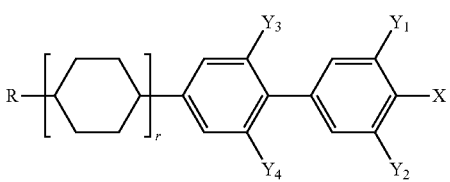
III
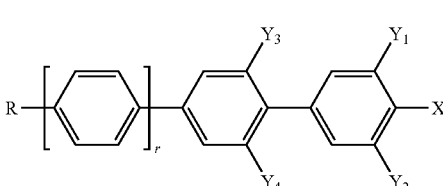
IV
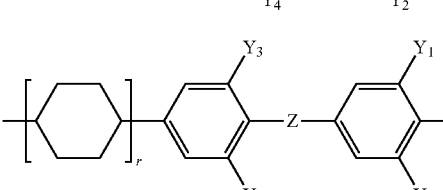
V
6. The mixture of claim 4, wherein the mixture further comprises at least one compound of formula XVII-XXIII:
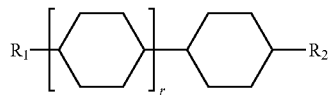
XVII
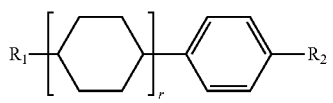
XVIII
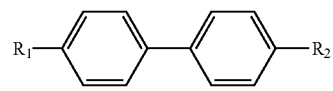
XIX
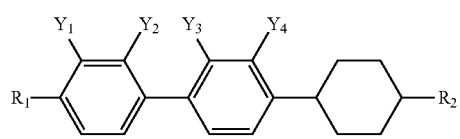
XX
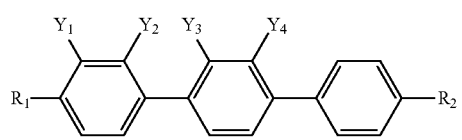
XXI
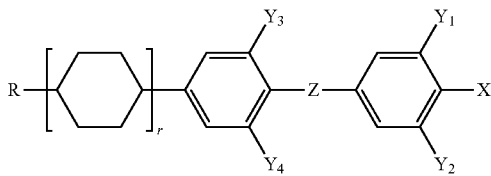
V
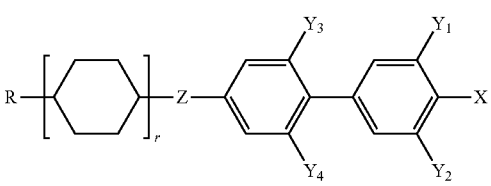
VI
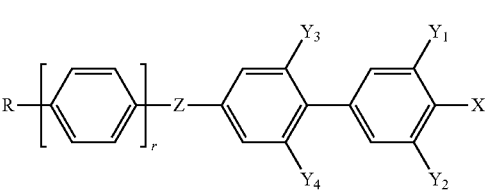
VII

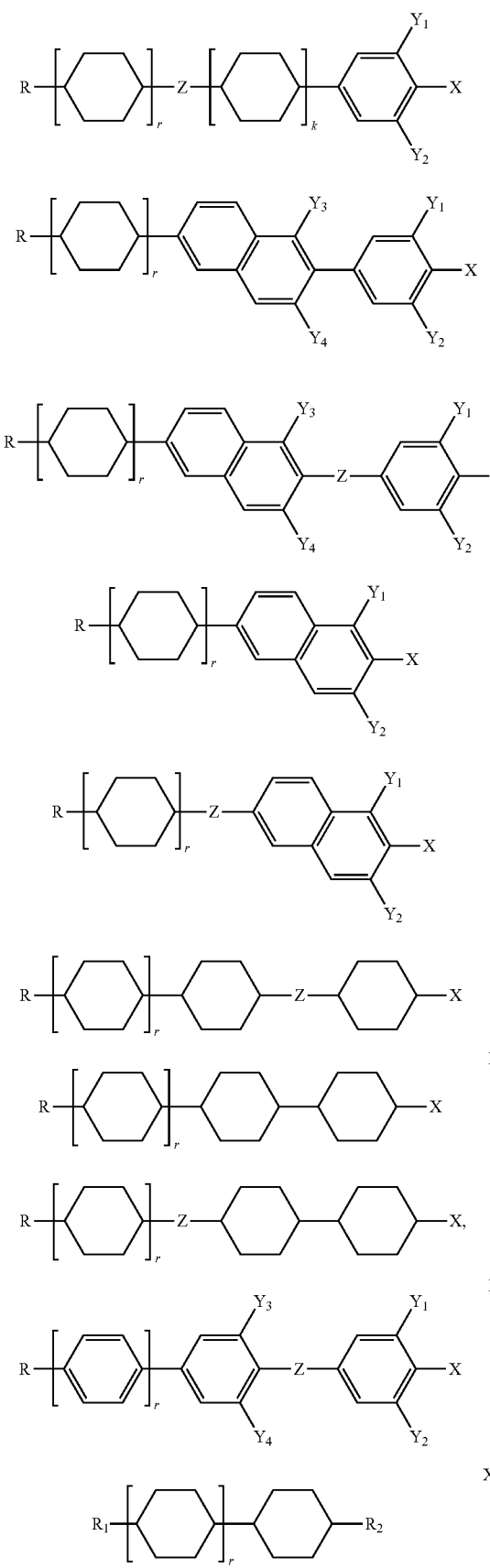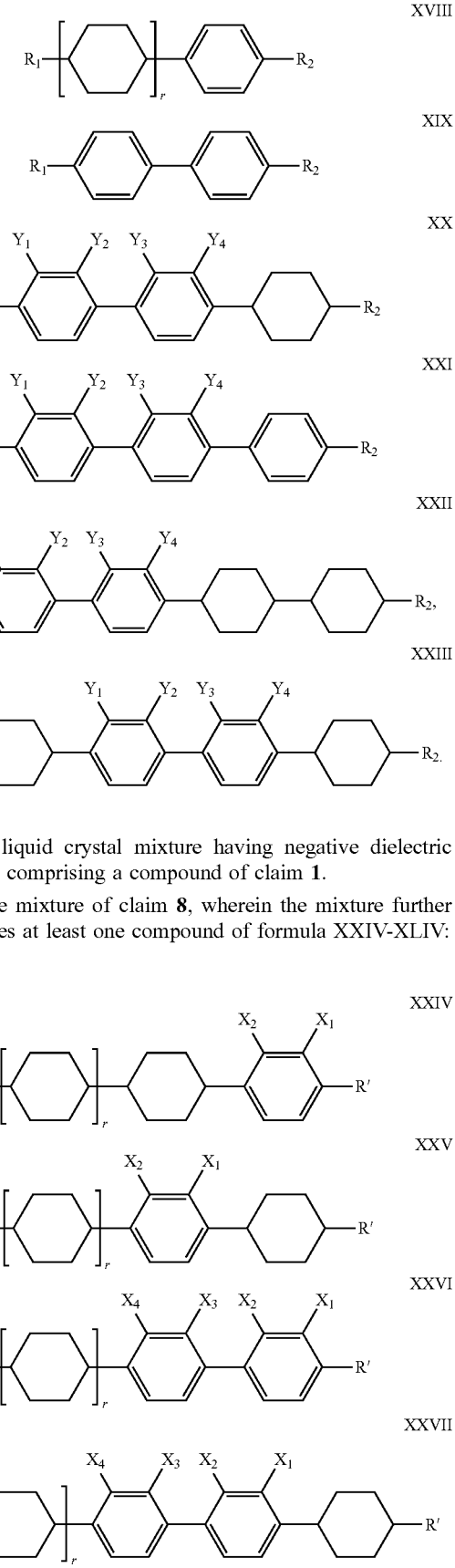
8. A liquid crystal mixture having negative dielectric constant comprising a compound of claim 1.
9. The mixture of claim 8, wherein the mixture further comprises at least one compound of formula XXIV-XLIV:

XXVIII
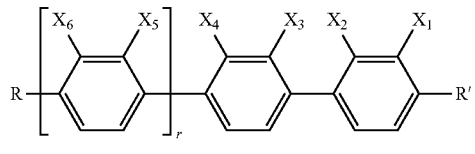
XXIX
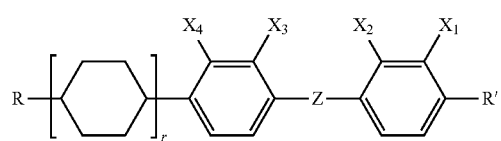
XXX
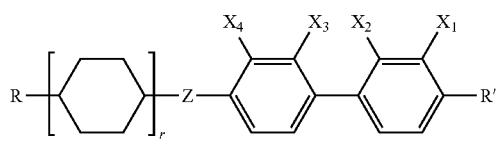
XXXI
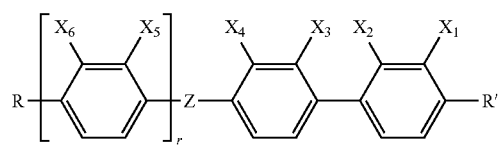
XXXII
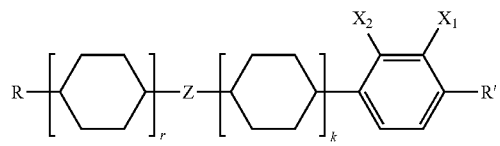
XXXIII
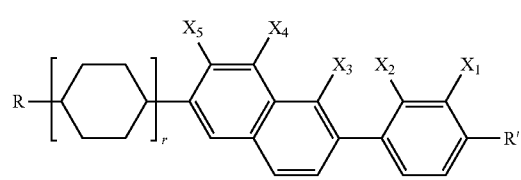
XXXIV
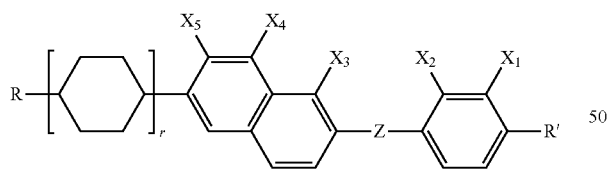
XXXV
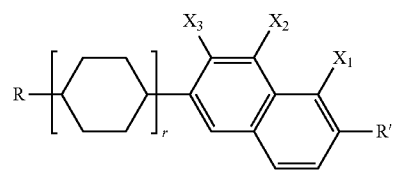
XXXVI
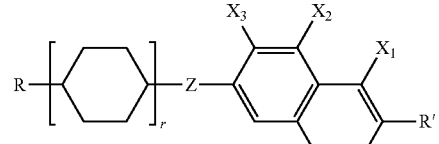
XXXVII
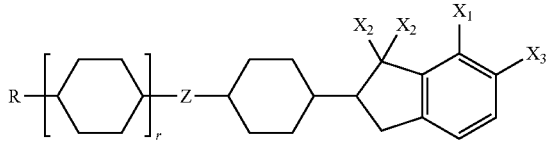
XXXVIII
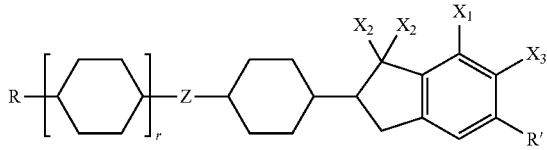
XXXIX
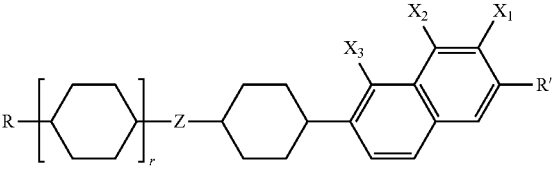
XL
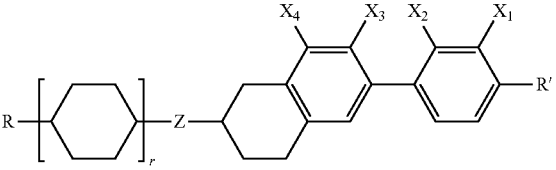
XLI
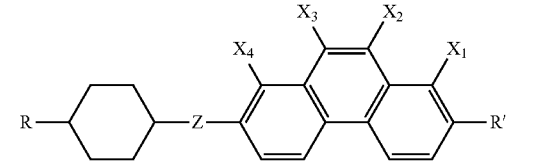
XLII
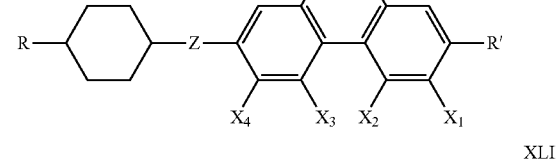
XLIII
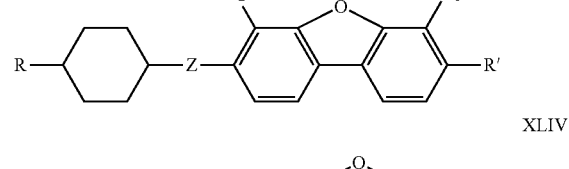
XLIV
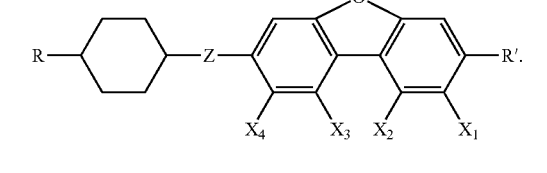
10. The mixture of claim 8, wherein the mixture further comprises at least one compound of formula XLV-XLVIII:

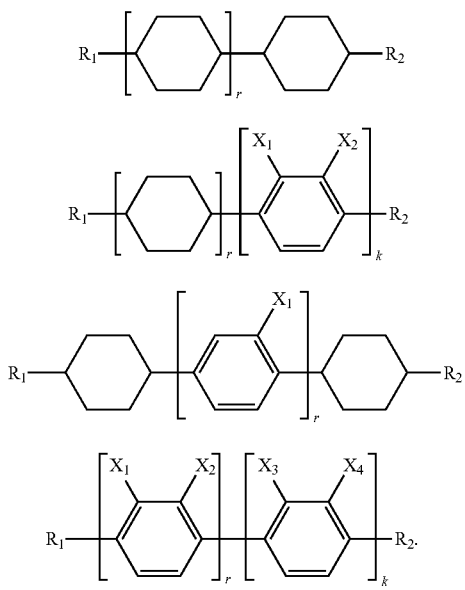
11. The mixture of claim 8, wherein the mixture further comprises at least one compound of formula XXIV-XLIV and at least one compound of formula XLV-XLVIII, wherein:
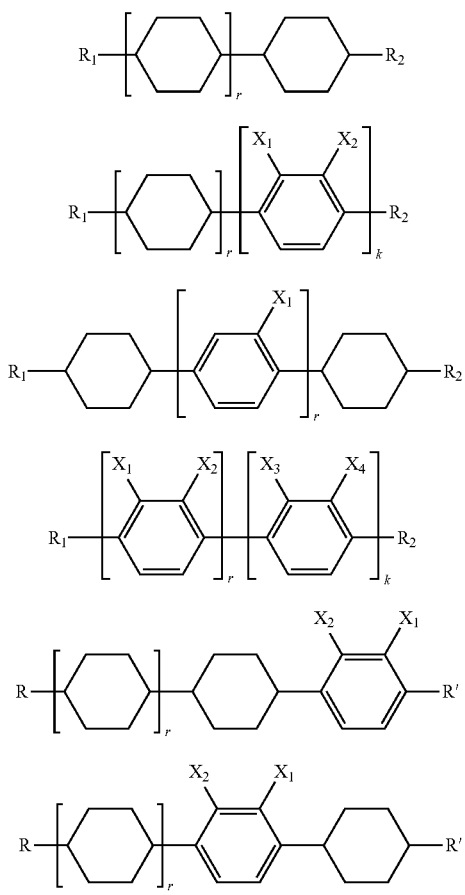
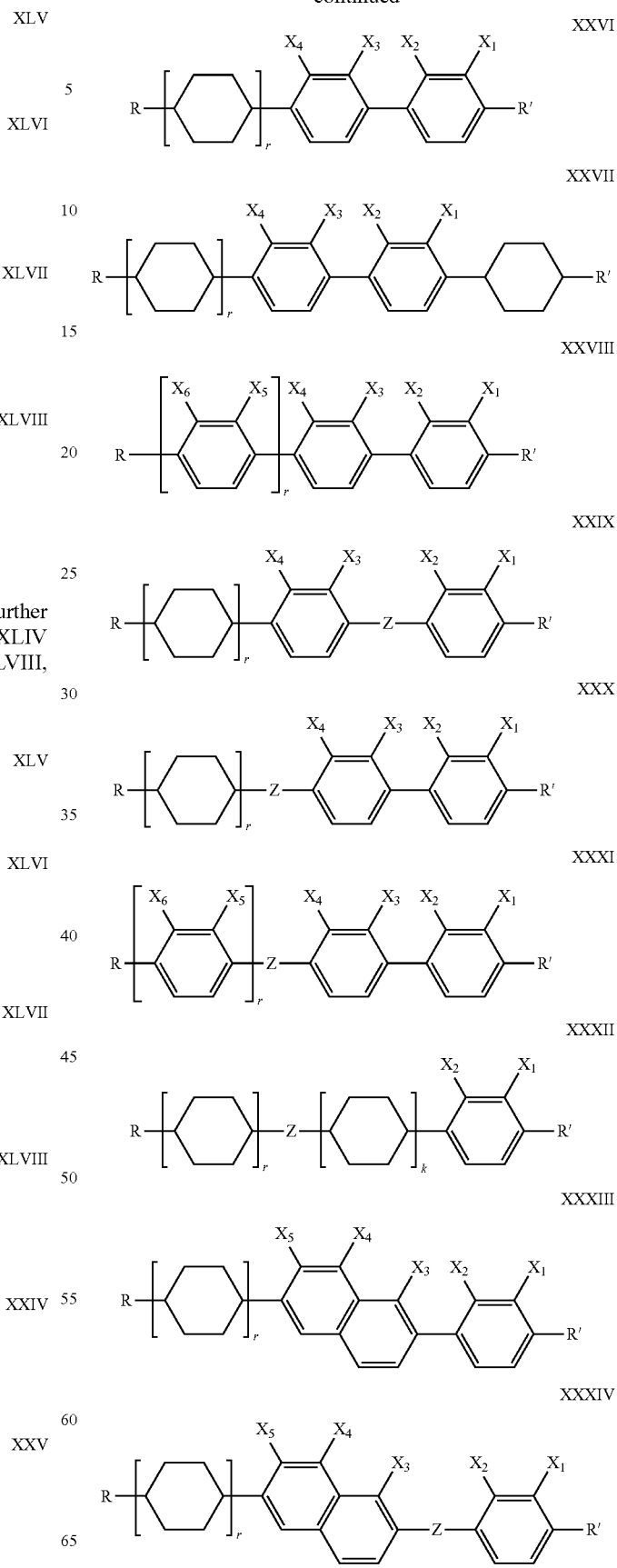

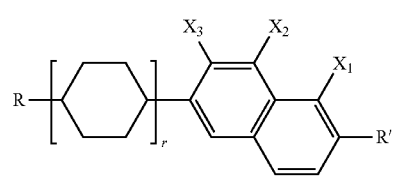 XXXV
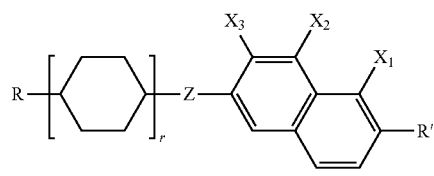 XXXVI
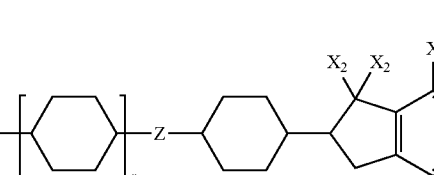 XXXVII
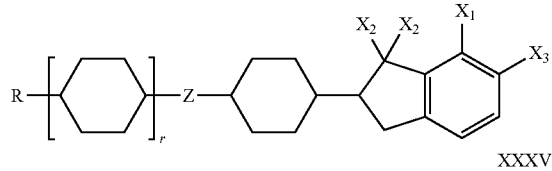 XXXVIII
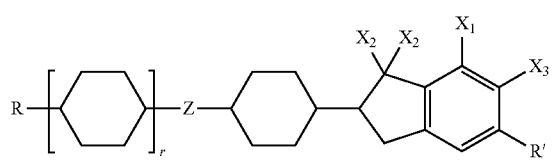 XXXIX
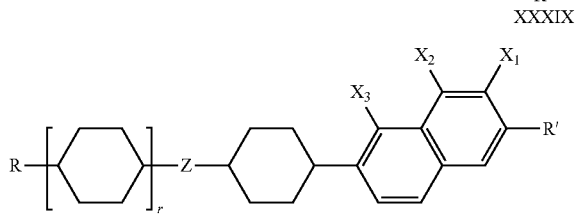 XL
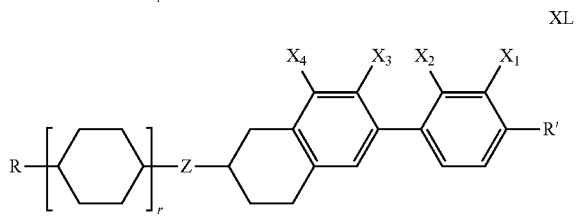 XL
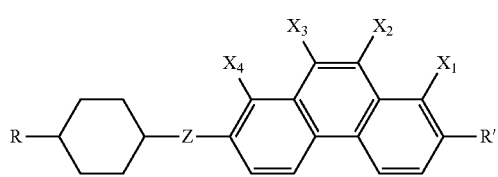 XLI
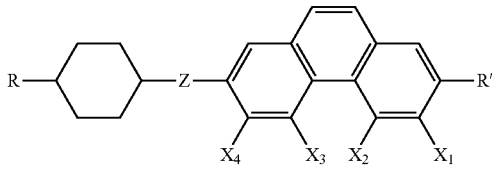 XLII
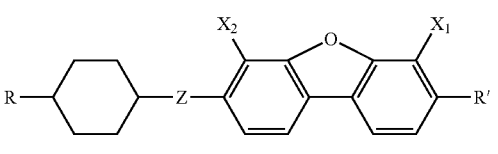 XLIII
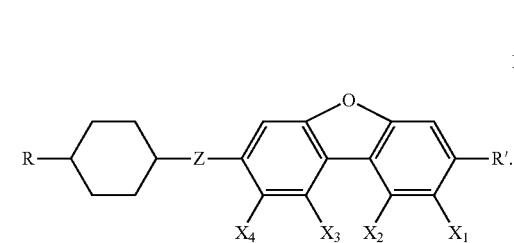 XLIV
12. A device comprising a compound of claim 1.
13. A device comprising a mixture of claim 3.
14. The compound of claim 1, wherein one or more hydrogen atoms in any ring is substituted with deuterium.
15. The compound of claim 1, wherein one or more hydrogen atoms in any non-ring structure is substituted with deuterium.
* * * * *